(12) United States Patent
Kojo

(10) Patent No.: US 11,998,285 B2
(45) Date of Patent: Jun. 4, 2024

(54) SURGICAL GUIDING PROBE

(71) Applicant: GYRUS ACMI, INC., Southborough, MA (US)

(72) Inventor: Hiroyuki Kojo, Brookline, MA (US)

(73) Assignee: Gyrus ACMI, Inc., Westborough, MA (US)

(*) Notice: Subject to any disclaimer, the term of this patent is extended or adjusted under 35 U.S.C. 154(b) by 471 days.

(21) Appl. No.: 17/108,244

(22) Filed: Dec. 1, 2020

(65) Prior Publication Data
US 2021/0169584 A1   Jun. 10, 2021

Related U.S. Application Data

(60) Provisional application No. 62/943,347, filed on Dec. 4, 2019.

(51) Int. Cl.
*A61B 34/20* (2016.01)
*A61B 1/018* (2006.01)
(Continued)

(52) U.S. Cl.
CPC .............. *A61B 34/20* (2016.02); *A61B 1/018* (2013.01); *A61B 8/0841* (2013.01); *A61B 8/085* (2013.01); *A61B 17/3478* (2013.01); *A61B 2017/00278* (2013.01); *A61B 2034/2057* (2016.02); *A61B 2034/2063* (2016.02);
(Continued)

(58) Field of Classification Search
None
See application file for complete search history.

(56) References Cited

U.S. PATENT DOCUMENTS 6,895,266 B1   5/2005   Hollis
2006/0241342 A1*  10/2006  Macaulay .......... A61B 17/3478
                                                     600/104
(Continued)

FOREIGN PATENT DOCUMENTS

CN          114746021 A       7/2022
WO     WO-2021113210 A1       6/2021

OTHER PUBLICATIONS

"International Application Serial No. PCT US2020 062655, International Search Report dated Mar. 11, 2021", 6 pgs.
(Continued)

*Primary Examiner* — Katherine L Fernandez
*Assistant Examiner* — Farouk A Bruce
(74) *Attorney, Agent, or Firm* — Schwegman Lundberg & Woessner, P.A.

(57) ABSTRACT

A guiding probe for identifying a location within an anatomical region of a patient. The guiding probe can optionally: a graspable portion, an insertion portion and an emitter. The insertion portion can be coupled to the graspable portion. The insertion portion can have an elongated extent and a longitudinal axis. The insertion portion can include a flexible section and a bending section. The bending section can be positioned distal of the flexible section. The emitter can be coupled to a distal end portion of the insertion portion. The emitter can be configured for use within the anatomical region to emit a signal that can be detectable extracorporeally of the patient whereby the signal enables the location within the anatomical region to be identified extracorporeally for therapy to be applied.

6 Claims, 7 Drawing Sheets

(51) Int. Cl.
*A61B 8/08* (2006.01)
*A61B 17/34* (2006.01)
*A61B 17/00* (2006.01)
*A61B 90/00* (2016.01)

(52) U.S. Cl.
CPC ............. *A61B 2090/3788* (2016.02); *A61B 2090/3929* (2016.02); *A61B 2090/3979* (2016.02)

(56) References Cited

U.S. PATENT DOCUMENTS

| | | | | |
|---|---|---|---|---|
| 2007/0282206 | A1* | 12/2007 | Arnone | G01N 21/3586 600/473 |
| 2008/0039715 | A1* | 2/2008 | Wilson | A61B 5/06 600/424 |
| 2008/0097218 | A1* | 4/2008 | Vrba | A61B 17/0057 600/465 |
| 2008/0319356 | A1* | 12/2008 | Cain | A61M 37/0092 600/300 |
| 2011/0015483 | A1* | 1/2011 | Barbagli | A61B 1/307 600/108 |
| 2012/0078103 | A1* | 3/2012 | Tashiro | A61B 8/5207 600/443 |
| 2013/0281834 | A1* | 10/2013 | Tashiro | A61B 8/145 600/424 |
| 2014/0094695 | A1 | 4/2014 | Jain et al. | |
| 2014/0275956 | A1 | 9/2014 | Fan | |
| 2017/0172539 | A1 | 6/2017 | Vignon et al. | |
| 2017/0186200 | A1* | 6/2017 | Utsunomiya | G06T 11/60 |
| 2018/0093076 | A1* | 4/2018 | Rauniyar | A61M 25/065 |

OTHER PUBLICATIONS

"International Application Serial No. PCT US2020 062655, Written Opinion dated Mar. 11, 2021", 6 pgs.

"International Application Serial No. PCT/US2020/062655, International Preliminary Report on Patentability dated Jun. 16, 2022", 8 pgs.

* cited by examiner

SURGICAL GUIDING PROBE

CROSS-REFERENCE TO RELATED APPLICATION

This application claims the benefit of priority to U.S. Provisional Patent Application Ser. No. 62/943,347, filed on Dec. 4, 2019, the contents of which are incorporated herein in their entirety.

TECHNICAL FIELD

This document pertains generally, but not by way of limitation, to surgical devices, and more particularly, to a surgical guiding probe having an emitter.

BACKGROUND

Various surgical techniques have been developed for treating kidney stones. Treatment can be performed endoscopically or laparoscopically, for example. Thus, depending on various factors including the size of the stone, the manner of treatment can be selected. If the kidney stone is greater than about 20 mm in diameter, the kidney stone will generally need to be positionally identified and then a planned percutaneous nephrostomy procedure can be performed. This procedure prepares for a percutaneous nephrolithotomy (PCNL) procedure where a percutaneous nephrolithotomy needle is extracorporeally positioned external of the patient. The needle is then inserted from the external location through the patient's back to the target location such as a calyx of the kidney. Various stone fragmentation devices and stone retrieval devices can then be utilized with the access pathway created by the needle.

PCNL relies on precise positioning to locate the targeted calyx (the particular surgical target) without disturbing nearby structures of the kidney that may adversely affect the surgical results. As such, it requires substantial skill. Failure to adequately locate and access the targeted calyx can result in multiple access attempts, injury to the kidney or adjacent organs, increased procedure time, increased cost spent on the procedure and post-treatment recovery and increased patient blood loss and the probability of complications.

Overview

The following examples and discussion illustrate various configurations of the disclosed approach. In one example configuration, the proposed approach uses an in vivo emitter and extracorporeal detector that facilitates a desired alignment of the percutaneous nephrolithotomy needle with the targeted calyx. The present inventor has recognized, among other things, that the foregoing challenges of adequately positionally identifying the targeted calyx and determining a proper extracorporeal position for the needle so that the needle is properly aligned with the targeted calyx can be improved with the use of an in vivo emitter and extracorporeal detector. Such a system and technique can provide for a quicker and more accurate percutaneous access to the targeted calyx. This, in turn, reduces the risk associated with radiation visualization, the time and cost spent on the procedure, patient blood loss due to multiple/faulty attempted access and the probability of complications due to multiple/faulty attempted access.

As used therein the term "signal" means radiant or electromagnetic energy of any type including but not limited to light (in any frequency or frequency range), sound signals (of any extracorporeally detectable type), or the like. A "signal" can be a controlled wave or controlled pulse, for example. Although not specifically discussed, it is understood that the "signal" may be focused and/or amplified by any known mechanism such as by a lens, antenna, amplifier, or the like.

Example 1 is a guiding probe for identifying a location within an anatomical region of a patient. The guiding probe can optionally: a graspable portion, an insertion portion and an emitter. The insertion portion can be coupled to the graspable portion. The insertion portion can have an elongated extent and a longitudinal axis. The insertion portion can include a flexible section and a bending section. The bending section can be positioned distal of the flexible section. The emitter can be coupled to a distal end portion of the insertion portion. The emitter can be configured for use within the anatomical region to emit a signal that can be detectable extracorporeally of the patient whereby the signal enables the location within the anatomical region to be identified extracorporeally for therapy to be applied.

Example 2 is the guiding probe of Example 1, wherein the emitter can be positioned at a distal tip of the insertion portion and can be configured to emit the signal along a linear pathway from the distal tip. The signal passes can pass through tissue of the patient including an epidermis along the linear pathway.

Example 3 is the guiding probe of Example 2, wherein the emitter can be aligned with the longitudinal axis of the insertion portion.

Example 4 is the guiding probe of any one or any combination of Examples 1-3, wherein the signal can comprise one of a light or an ultrasonic sound signal.

Example 5 is the guiding probe of Example 4, wherein the light can have one of a frequency range of about 430 THz to about 770 THz or about 300 GHz to about 430 THz.

Example 6 is the guiding probe of any one or any combination of Examples 1-5, wherein the location within the anatomical region can comprise a calyx of a kidney of the patient and further comprising a needle configured to perform a percutaneous access incision to the calyx.

Example 7 is the guiding probe of any one of Examples 1-6, wherein the guiding probe can comprise an endoscope or can be passed through a working channel of the endoscope.

Example 8 is a system for identifying a location within an anatomical region of a patient. The system can optionally comprise a guiding probe and a detection device. The guiding probe can optionally comprise a graspable portion, an insertion portion and an emitter. The insertion portion can be coupled to the graspable portion. The insertion portion can have an elongated extent and a longitudinal axis. The insertion portion can include a flexible section and a bending section. The bending section can be positioned distal of the flexible section. The emitter can be configured to couple to a distal end portion of the insertion portion. The emitter can be configured for use within the anatomical region to emit a signal. The detection device can be extracorporeal of the patient and can be configured to detect the signal emitted within the anatomical region, whereby the signal when detected enables the location within the anatomical region to be identified extracorporeally for therapy to be applied.

Example 9 is the system of Example 8, wherein the signal can comprise light and the detection device can comprise a camera configured to detect the light emitted from an epidermis of the patient.

Example 10 is the system of Example 9, wherein the camera can be configured to detect light in a frequency range of about 300 GHz to about 430 THz.

Example 11 is the system of Example 8, wherein the signal can comprise an ultrasonic sound signal and the detection device can comprise an ultrasound device.

Example 12 is the system of any one of Examples 8-11, optionally further comprising a signal generator that can be configured to produce the signal. The signal generator can be coupled to the emitter via a pathway through the working channel.

Example 13 is the system of any one or any combination of Examples 8-12, wherein the emitter can be positioned at a distal tip of the insertion portion and can be configured to emit the signal along a linear pathway from the distal tip. The linear pathway can extend from the distal tip through tissue of the patient including an epidermis.

Example 14 is the system of Example 13, wherein the emitter can be aligned with the longitudinal axis of the insertion portion and the guiding probe can comprise an endoscope or can be passed through a working channel of the endoscope.

Example 15 is the system of any one of Examples 8-14, optionally further comprising an access needle having a shaft and a tip located at a distal end of the shaft. The access needle can be configured for a percutaneous access incision. The location within the anatomical region can comprises a calyx of a kidney of the patient.

Example 16 is a method of detecting an emitter within an anatomical region. The method can optionally comprise: emitting a signal from a guiding probe while positioned at a desired location within the anatomical region; detecting the signal extracorporeally; and determining an extracorporeal location aligned with the desired location based upon a location of the detected extracorporeal signal and based upon a linear pathway for the signal from the desired location to the extracorporeal location.

Example 17 is the method of Example 16, wherein the extracorporeal location can comprise a position on a dermis.

Example 18 is the method of any one or any combination of Examples 16-17, optionally further comprising accessing the desired location derived from the signal by puncturing through tissue from the extracorporeal location.

Example 19 is the method of any one of Examples 16-18, optionally further comprising superimposing the signal once detected as a line on an ultrasonic image and displaying the image on a display.

Example 20 is the method of Example 19, optionally further comprising determining the extracorporeal location of the signal with reference to the display and a location of an ultrasound probe.

Example 21 is any one or any combination of Examples 1-21 or elements thereof.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

The present disclosure is directed to a surgical device comprising a guiding probe and related systems and methods. Although described in reference to PCNL for treatment of kidney stones, it should be recognized that the apparatuses, systems, methods and techniques of the present application are not limited to this type of procedure. Indeed, the present apparatuses, systems, methods and techniques can be utilized in any procedure that relies on precise positioning to a particular surgical target without disturbing nearby anatomical structures.

In this disclosure, relative terms, such as, for example, "about", "generally", or "substantially" are used to indicate a possible variation of ±10% in a stated numeric value or within ±10° of the numeric value.

Figure 1:
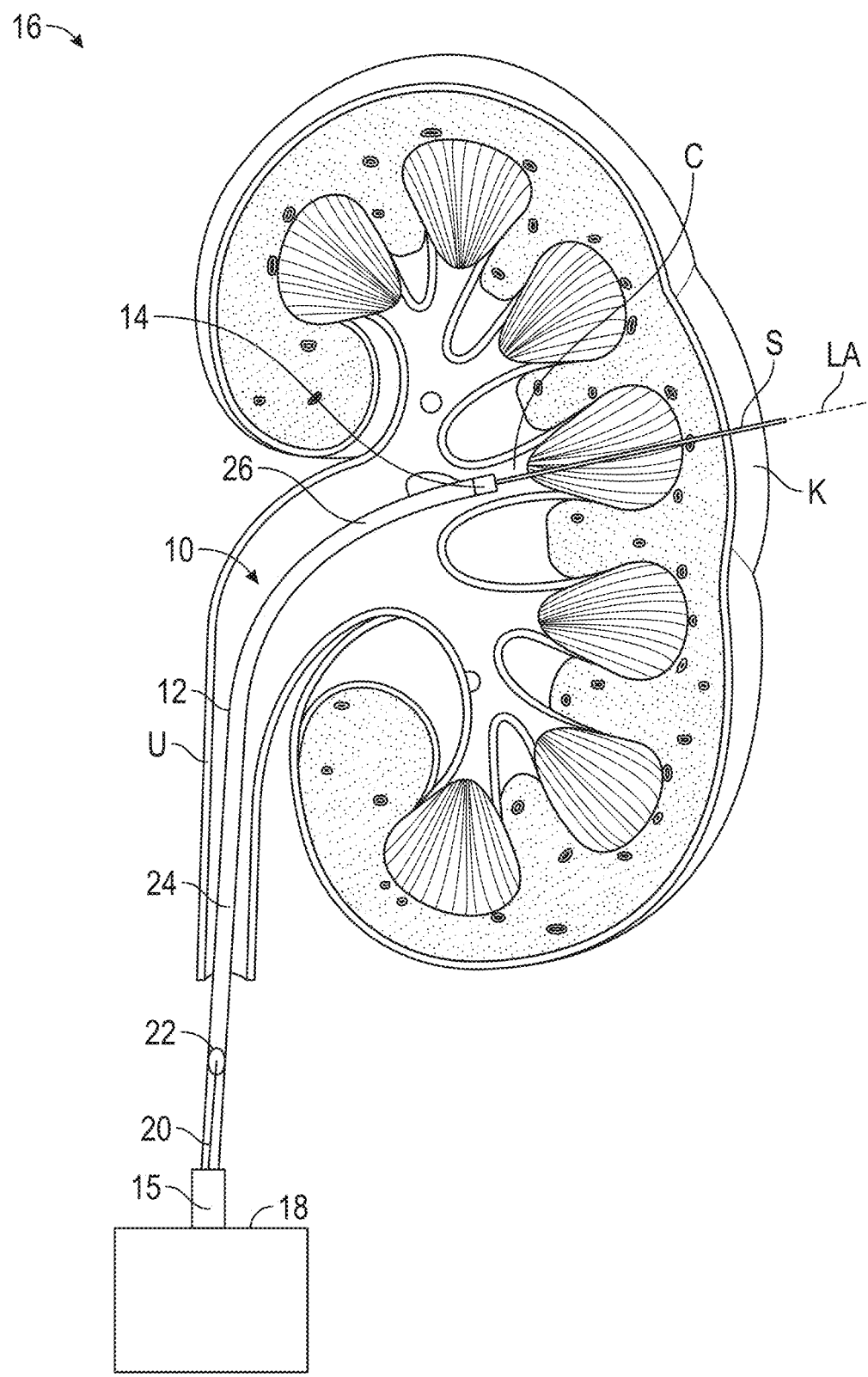
FIG. 1 is a schematic view of a guiding probe for identifying a location within an anatomical region of a patient according to an example the present application.

FIG. 1 is a schematic diagram of a guiding probe 10 being manipulated within a kidney K of a patient according to an example of the present application. The guiding probe 10 can include an insertion portion 12 and an emitter 14. The guiding probe 10 can include other portions such as a graspable portion 15 and/or actuator(s) (not shown). The guiding probe 10 can be used as part of a system 16 that includes a signal generator 18 and a signal pathway 20.

As illustrated in FIG. 1, the guiding probe 10 can be configured to access the kidney K via a ureter U and can be manipulatable within the kidney K to emit a signal S used to identify an in situ target location (sometimes referred to simply as a target location or a location herein) that can comprise an anatomy such as a calyx C for access by a needle (not shown) to treat a kidney stone. This target location can be correlated to an extracorporeal puncture location on a dermis. The insertion portion 12 can be configured as a tube or shaft having an elongated extent and a longitudinal axis LA. The insertion portion 12 can provide a working channel 22 such as for the signal pathway 20 and other components such as an actuator to manipulate the distal end portion of the guiding probe 10.

To access the kidney K via the ureter U, the insertion portion 12 can be appropriately sized and can have a flexible section 24. The insertion portion 12 can also have a bending section 26 distal of the flexible section 24. The bending section 26 can be configured to be manipulatable to bend within and adjacent the kidney K as illustrated in FIG. 1 to position the distal tip of the probe 10 within, aligned with or adjacent one or more of the calyx C, for example. One of the one or more calyx C can be the target location for the needle of the PCNL as previously described and can be selected based upon the location of the kidney stone(s). Positioning of the probe 10 within the kidney K and at the target location (e.g., aligned with or adjacent one or more of the calyx C) can be facilitated by endoscopic imaging and with the support of X-ray imaging, for example.

The emitter 14 can be coupled to the insertion portion 12 such as by being positioned around a circumference of or within a distal end portion of the bending section 26. Thus, the emitter 14 can be positioned at or adjacent the distal tip of the guiding probe 10 and can be configured to emit a signal S that is aligned with the longitudinal axis LA of the insertion portion 12, for example. As discussed in further detail subsequently, the signal S can be, but is not limited to visible light, infrared light, or sound signals such as an ultrasonic sound signals. The signal S can be of a sufficient amplitude to be detectable extracorporeally as is further discussed subsequently. As discussed subsequently, the detected signal can be used to identify the target location and can be used to identify an appropriate extracorporeal location on a dermis of the patient that is linearly aligned with the target location.

The guiding probe 10 can be part of the aforementioned system 16. The signal generator 18 can be a separate device or can be coupled to and/or be part of the guiding probe 10. The signal generator 18 can be configured to generate the signal S that is carried via the signal pathway 20 along the insertion portion 12 to the emitter 14.

Figure 2:
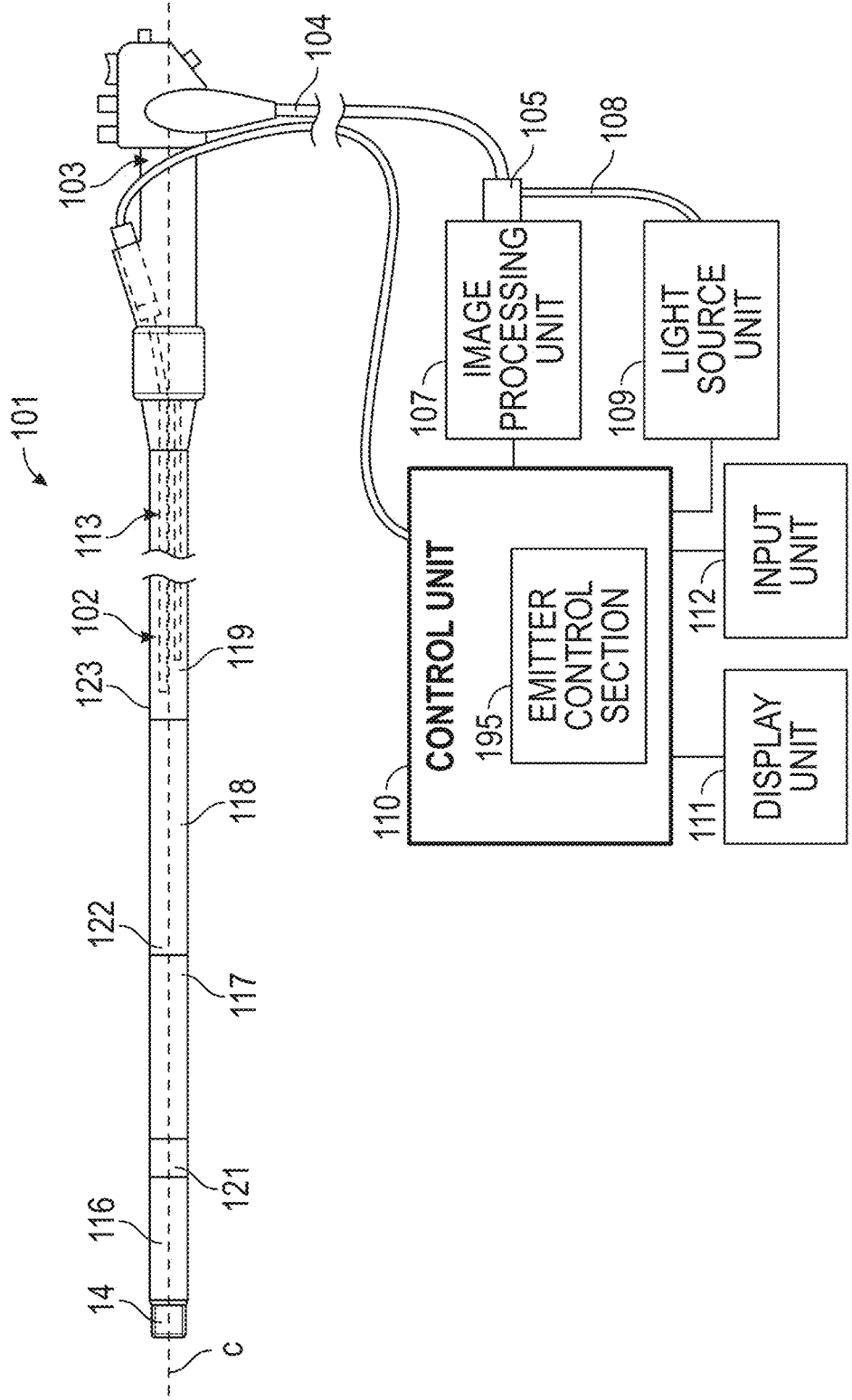
FIG. 2 is a schematic view of an endoscope configured as a guiding probe for identifying a location within the anatomical region of the patient according to an example the present application.

FIG. 2 shows an example of an endoscope 101 that can be configured as the guiding probe as previously discussed in reference to FIG. 1 or could be utilized in conjunction with the guiding probe of FIG. 1. Thus, for example the endoscope in some examples can be a separate device from the guiding probe and can be configured to provide an access pathway for the insertion portion 12 and the emitter 12. FIG. 2 is an example where the endoscope 101 comprises the guiding probe. The endoscope 101 can be used with the system 16 (e.g., a separate generator device, for example) as previously described. It should be noted that although the endoscope 101 of FIG. 2 is described as having certain components and features, these are optional and need note be present in all examples. The guiding probe as previously discussed and illustrated does not need these components and features. Thus, for example, the endoscope need not have visualization/imaging capability as further described with reference to the example of FIG. 2.

As shown in FIG. 2, the endoscope 101 can include an insertion section 102, and an operation section 103. The operation section 103 can be provided to a proximal direction side of the insertion section 102. The insertion section 102 can be configured to be inserted into a vessel of the patient. One end of a universal cable 104 can be connected to the operation section 103. A scope connector 105 can be provided at the other end of the universal cable 104. The scope connector 105 can be connected to an image processing unit 107 such as an image processor. One end of a light guide tube 108 can be connected to the scope connector 105. The other end of the light guide tube 108 can be connected to a light source unit 109.

The image processing unit 107 and the light source unit 109 can be electrically connected to a control unit 110 such as a personal computer configured to control the entire system of the endoscope 101. Furthermore, a display unit 111 such as a monitor and an input unit 112 such as a keyboard or a mouse can be electrically connected to the control unit 110.

The insertion section 102 can include an elongated insertion main body 113 which can be extended along a longitudinal axis C. The insertion main body 113 can include the emitter 14 provided on a distal end portion, an active bending portion 116 provided to a proximal direction side of the emitter 14, a passive bending portion 117 that can be provided to the proximal direction side of the active bending portion 116 and configured to passively bend upon being subject to an external force, a first flexible portion 118 can be provided to the proximal direction side of the passive bending portion 117, and a second flexible portion 119 can be provided to the proximal direction side of the first flexible portion 118. The active bending portion 116 can be connected to the passive bending portion 117 through a bending tube connecting portion 121. Moreover, the passive bending portion 117 can be connected to the first flexible portion 118 through an intermediate connecting portion 122. Additionally, the first flexible portion 118 can be connected to the second flexible portion 119 through a flexible tube connecting portion 123.

The endoscope 101 can have various motorized movement and/or imaging capabilities as known in the art. Thus, the endoscope 101 can have a motor 175 according to some examples to manipulating the bending portion 117, for example. The endoscope 101 can have an image processing unit 107 configured to detect brightness of an image of a subject. The control unit can include various units (also termed sections). Such units can include a directional relationship detection section configured to detect a relationship between an insertion direction of the insertion section 102 and an extending direction of the lumen based on various criteria including detection result in a brightness detection section. The units can include a motor control section that can be configured to control rotational drive of the motor 175 based various criteria. The control unit 110 can include an emitter control section 195 configured to control operation of the emitter 14 to actuate the signal S (FIG. 1), for example. The emitter control section 195 can be operably linked or otherwise related with one or more of the various units or criteria as desired.

Figure 3:
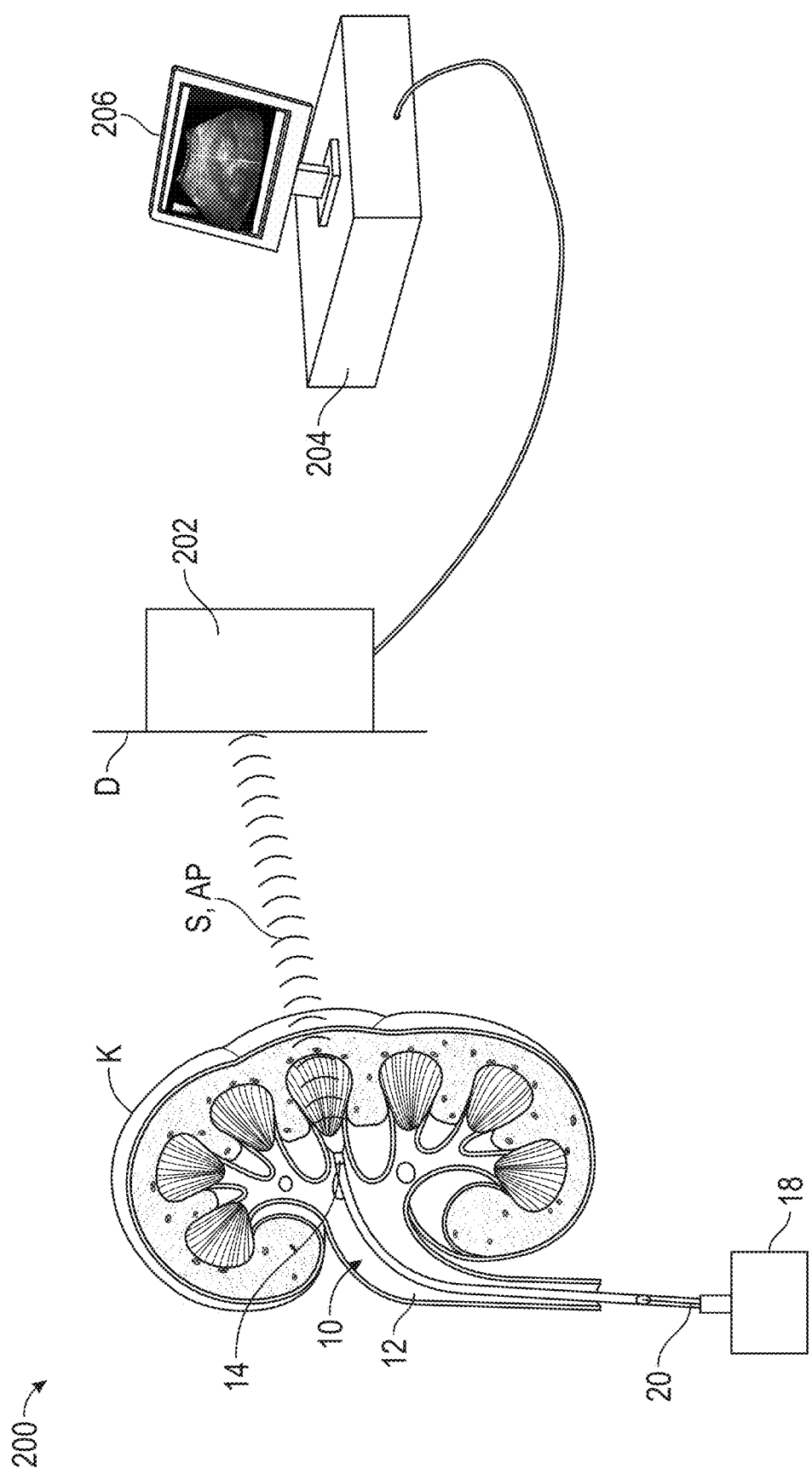
FIG. 3 is a schematic view of a system including the guiding probe and an extracorporeal detector according to an example of the present application.

FIG. 3 shows a schematic view of a system 200 for identifying a location (here at, adjacent or aligned with a calyx C) within an anatomical region (here the kidney K) of the patient. The system 200 can include the guiding probe 10 as previously discussed having the insertion portion 12 and the emitter 14 and a detection device 202, a computer 204 and a display 206.

As shown in FIG. 3, the detection device 202 can be located extracorporeal of the patient such as abutting or spaced from a dermis D thereof. The detection device 202 can be configured to detect the signal S emitted within the anatomical region. This can be done by operation of the computer 204. The detection device 202 can be operably electronically coupled with the computer 204 and the display 206 to process the output of the detection device 202 and provide a surgeon or other user with desired data including a visual image on the display 206 of the signal S detected by the detection device 202 corresponding to the location of the signal S in situ. According to various examples, the detection device 200 can be an ultrasound device configured to detect ultrasonic sound signals from the emitter 14, a human eye that can be configured to detect visible light such as passing through the dermis D, or a camera configured to detect light such as infrared light. Each of these various detection devices are illustrated and discussed subsequently.

As discussed previously, the system 200 can include the signal generator 18 configured to produce the signal S and the pathway 20 through the working channel of the insertion portion 12. As discussed previously, the emitter 14 can be aligned or otherwise configured to emit the signal S so the signal S is aligned with the longitudinal axis of the insertion portion 12. The emitter 14 can be positioned at a distal tip of the insertion portion 12 and can be configured to emit the signal S along an access pathway AP from the distal tip. Indeed, the access pathway AP for the signal S is utilized herein for correlating the extracorporeal location for needle puncture with the in situ location. As illustrated in FIG. 3, the access pathway AP can be substantially linear in nature and can extend from the distal tip/emitter 14 at the in situ location through tissue including the kidney K of the patient and through the dermis D to be detected by the detection device 202.

Figure 4:
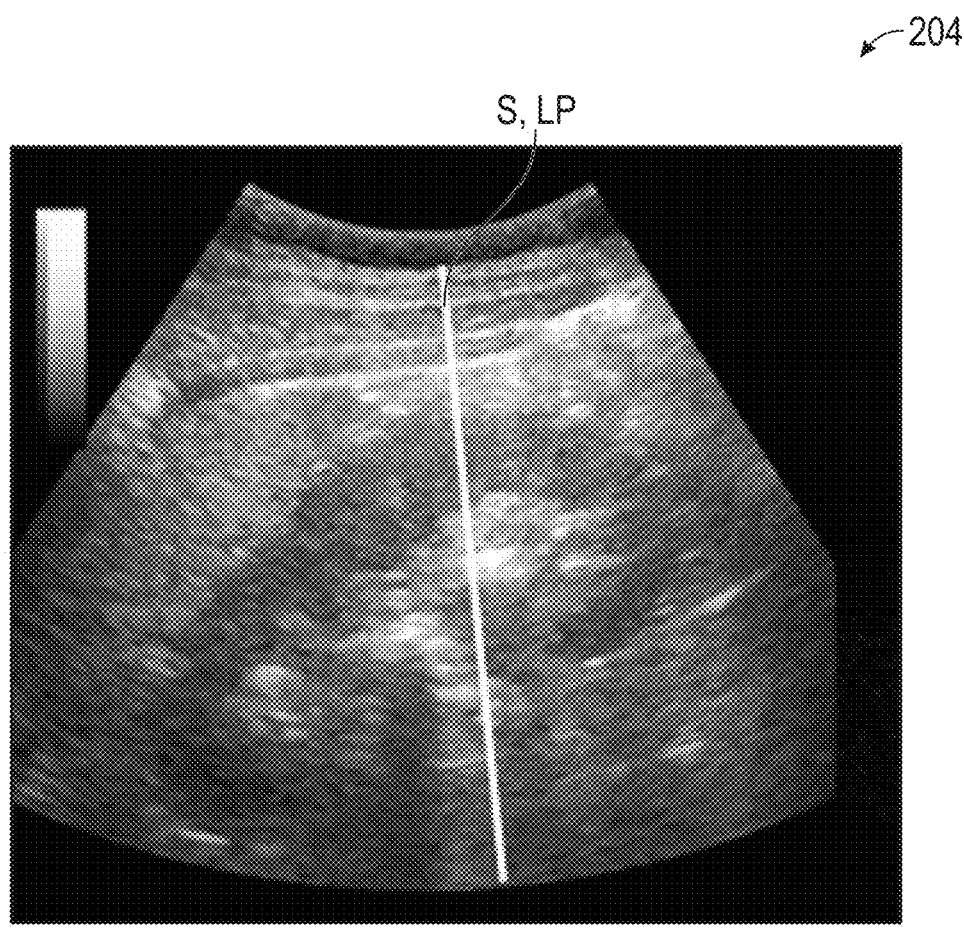
FIG. 4 is an ultrasound image of tissue and ultrasonic sound signals having a linear pathway according to an example of the present application.

FIG. 4 shows the display 204 displaying an image developed using an ultrasound device. The image shows the access pathway AP of the signal S (here ultrasonic sound signals) as a line on the image. The line can allow the surgeon to visual the access pathway to the location (e.g. the desired calyx) from an extracorporeal location. Put another way, the emitted ultrasonic sound signals can be superimposed on an anatomical map or image to provide the surgeon information on the location and a proper puncture location for access to the location. The map or image may be generated apriori using a previous image (e.g., generated using known imaging techniques and modalities such as contrast, ultrasound, etc.)

Figure 5:
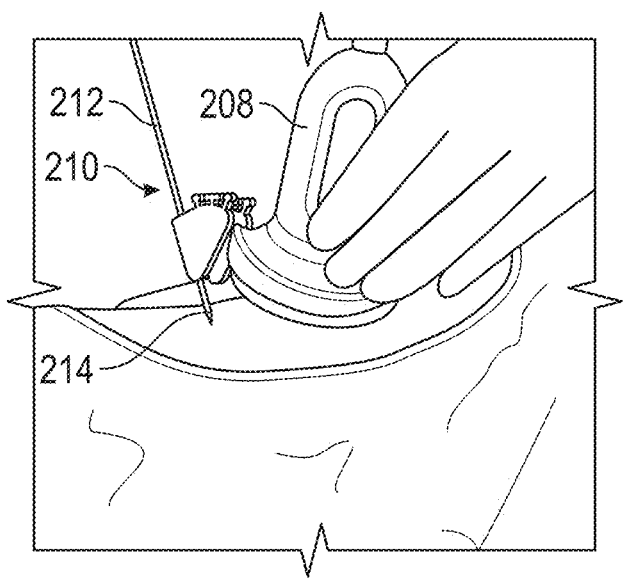
FIG. 5 is a first ultrasound probe configured to facilitate alignment and puncture of a needle for PCNL according to an example the present application.

FIG. 5 shows an ultrasound probe 208 according to a first example. The probe 208 can be configured to couple with and mount or otherwise retain an access needle 210 having a shaft 212 and a tip 214 located at a distal end of the shaft. The access needle 210 can be configured for a percutaneous access incision as part of the PCNL as discussed previously. It should be noted with the probe 208 configuration of FIG. 5, the surgeon can use linear pathway of the signal S (the line in FIG. 4) to support identification of the place to puncture with the needle 210. However, with the configuration of the probe 208 in FIG. 5, the surgeon, may not be able to puncture along the line directly with the probe 208 maintained in a position to display the line. Rather, alternatives such as marking the dermis with an estimate location of the line, estimating the extracorporeal location through slight or known distance shifting of the probe, or puncturing adjacent the line, can be employed.

Figure 6A:
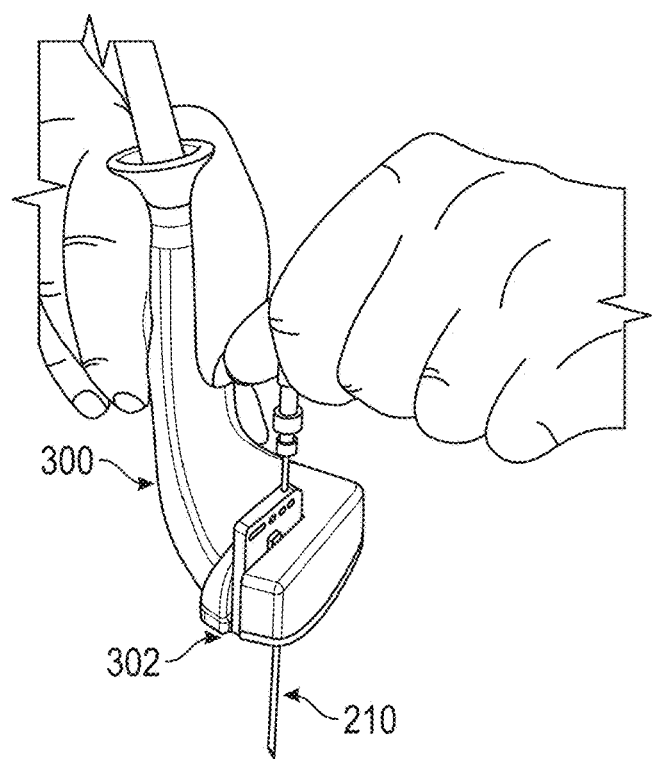
FIGS. 6A and 6B show a second ultrasound probe configured to facilitate alignment and puncture of the needle for the PCNL according to an example the present application.
Figure 6B:
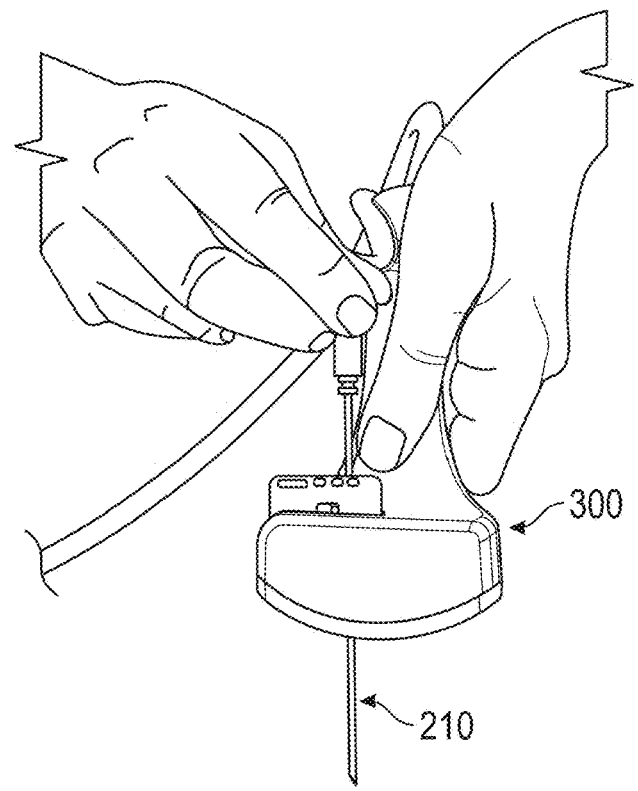

FIGS. 6A and 6B provide an example of an ultrasound device, specifically an ultrasonic probe 300 thereof that can be configured with an aperture 302 (FIG. 6A) to facilitate the locating and puncture with the needle 210. With the ultrasonic probe 300 configuration of FIGS. 6A and 6B, the needle 210 can be aligned with the line for puncturing without having to utilize the alternatives employed with the device of FIG. 5.

Figure 7:
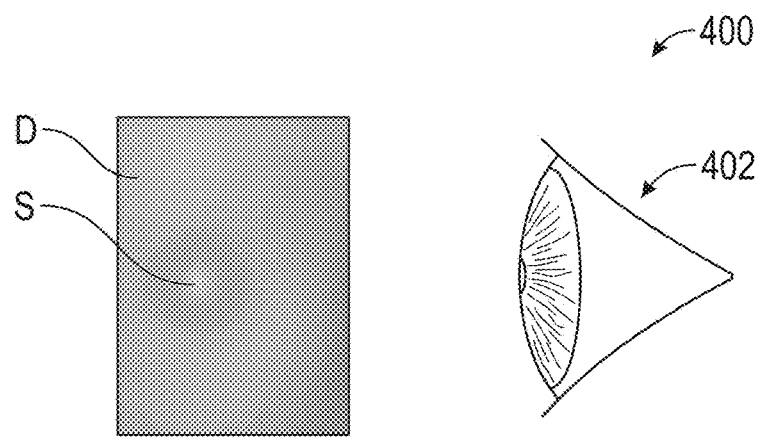
FIG. 7 is a schematic view of a system where the guiding probe emits light in a visible frequency range and having an amplitude that is extracorporeally visible to a human eye according to an example of the present application.

FIG. 7 shows a system 400 where the signal S of the in vivo emitter is light of a frequency range of about 430 THz to about 770 THz. Thus, the signal S can be emitted with a sufficient amplitude to travel through tissue and is in the frequency range to be visible to a human eye 402. The signal S (here light) following the linear pathway previously discussed and illustrate can pass through tissue and can indicate the location on the dermis D for puncture. This location on the dermis D can provide for a proper alignment and access to the location of the emitter. Human tissue is light diffusive, thus, the signal S can be visible through the human body including the dermis D. According to some examples, a material to aid in visualization of the linear pathway of the light can be utilized. For example, a light diffusing material (diffusive semi-transparent gel, smoke) can be placed upon the dermis D or extracorporeally adjacent the dermis D to aid in visualization.

Figure 8:
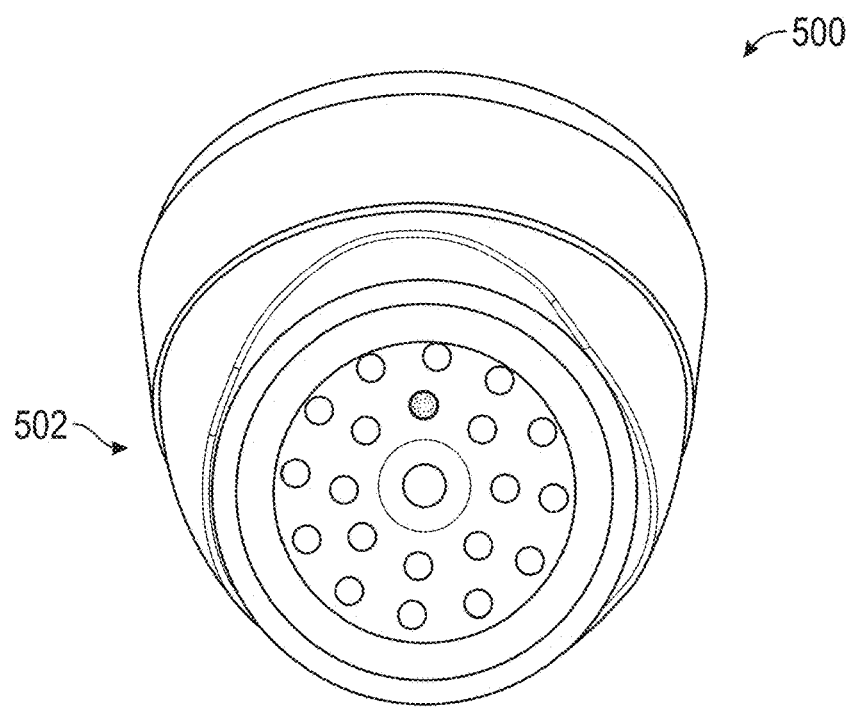
FIG. 8 is a schematic view of a system where the guiding probe emits light of a frequency range and amplitude that is captured by an extracorporeally located camera according to an example of the present application.
Figure 8:
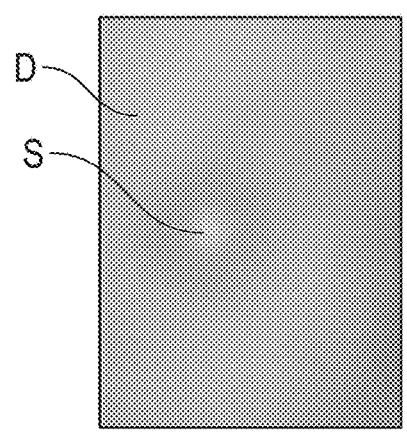

FIG. 8 shows a system 500 where the signal S of the in vivo emitter is light of a frequency range outside the visible frequency range. Thus, the signal S can be infrared light having a frequency range of about 300 GHz to about 430 THz, for example. The system 500 can include a camera 502 configured to capture light in the appropriate frequency range (here about 300 GHz to about 430 THz). The camera 502 or another device can then be configured to display the image captured by the camera 502 to a surgeon. Infrared light has good transparency through human tissue and can be observed by the infrared sensitive camera 502. According to some examples of the system 500 of FIG. 8, the material can be used to aid in visualization of the linear pathway of the light.

Figure 9:
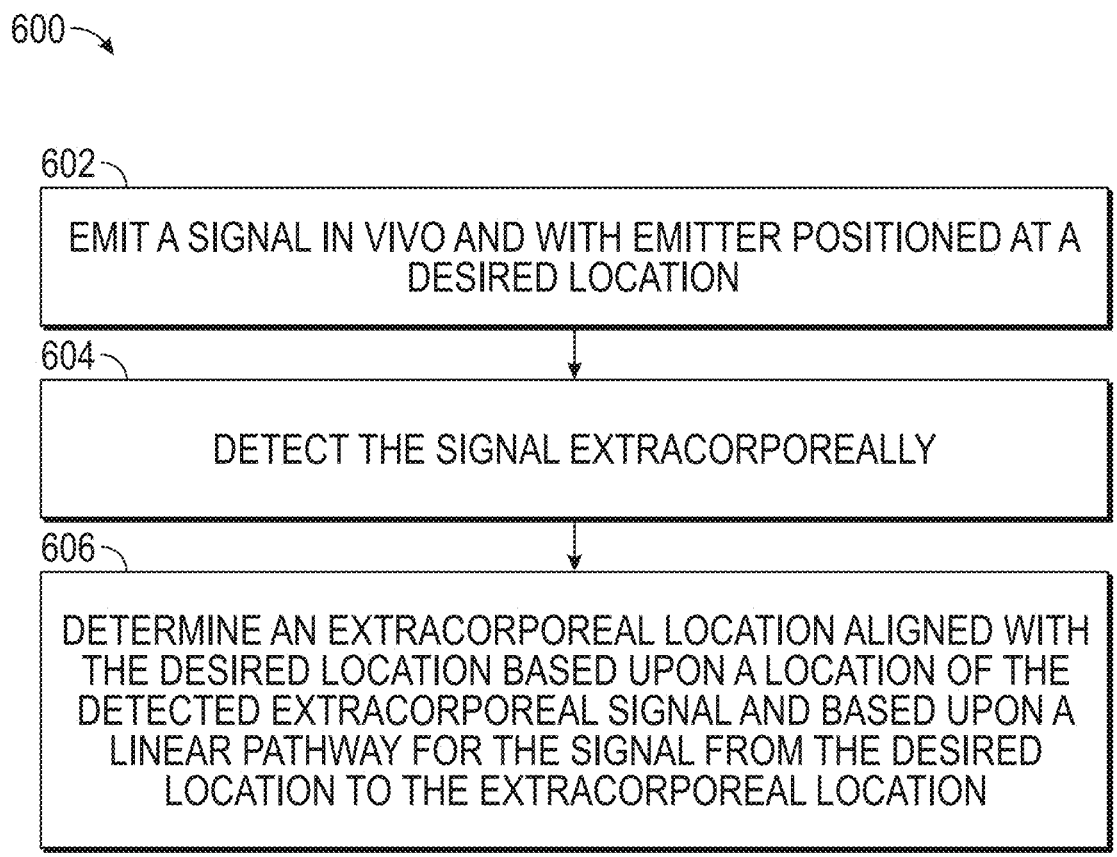
FIG. 9 is a method of detecting a guiding probe in vivo according to an example of the present application.

FIG. 9 shows a method 600 of detecting an emitter of a guiding probe in vivo according to an example. The method 600 can emit 602 a signal from the guiding probe while in vivo and positioned at a desired location. The method 600 can detect 604 the signal extracorporeally. The method 600 can determine 606 determining an extracorporeal location aligned with the desired location based upon a location of the detected extracorporeal signal and based upon a linear pathway for the signal from the desired location to the extracorporeal location. The method 600 can optionally include wherein the probe is an endoscope and the signal is emitted from a distal tip location of the endoscope. The method 600 can further include accessing the identified position of the signal in vivo by puncturing through tissue from the extracorporeal location. The signal can comprise one of light or ultrasonic sound signals of a sufficient amplitude to be detectable extracorporeally. The extracorporeal location can comprise a position on a dermis. The method 600 can superimpose the signal once detected as a line on an ultrasonic image and displaying the image. The method 600 can determine the extracorporeal location of the signal with reference to the display and a location of an ultrasound probe.

Various Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for identifying a location within an anatomical region of a patient, the system comprising:
    a display;
    a guiding probe comprising: a graspable portion;
    an insertion portion coupled to the graspable portion, the insertion portion having an elongated extent and a longitudinal axis, wherein the insertion portion includes a flexible section and a bending section, wherein the bending section is positioned distal of the flexible section; and
    an emitter coupled to a distal end portion of the insertion portion, the emitter configured for use within the anatomical region to emit an ultrasonic sound signal, wherein the emitter is positioned at a distal tip of the insertion portion and is configured to emit the ultrasonic sound signal along a linear pathway from the distal tip, wherein the linear pathway extends from the distal tip through tissue of the patient including an epidermis; and
    an ultrasound device extracorporeal of the patient and configured to detect the ultrasonic sound signal emitted within the anatomical region, whereby the ultrasonic sound signal when detected enables the location within the anatomical region to be identified extracorporeally and the ultrasound device positioned relative to the anatomic region;
    an access needle having a shaft and a tip located at a distal end of the shaft, wherein the access needle is configured for a percutaneous access incision;
    a processor configured to superimpose the ultrasonic sound signal as a line on an ultrasonic image displayed on the display,
    wherein the line is displayed prior to the percutaneous access incision and the access needle is configured to be positioned using the displayed line,
    wherein the ultrasound device includes one or more features for guiding the access needle during the percutaneous access incision.

2. The system of claim 1, further comprising a signal generator configured to produce the ultrasonic sound signal, wherein the signal generator is coupled to the emitter via a pathway through the working channel.

3. The system of claim 1, wherein the emitter is aligned with the longitudinal axis of the insertion portion and the guiding probe comprises an endoscope or is passed through a working channel of the endoscope.

4. The system of claim 1, wherein the location within the anatomical region comprises a calyx of a kidney of the patient.

5. A method of detecting an emitter within an anatomical region, the method comprising:
    emitting an ultrasonic sound signal from a guiding probe that is positioned at a desired location within the anatomical region, wherein the anatomical region is a kidney;
    detecting the ultrasonic sound signal extracorporeally;
    superimposing the ultrasonic sound signal once detected as a line on an ultrasonic image and displaying the image on a display;
    determining an extracorporeal location aligned with the desired location based upon a location of the detected extracorporeal ultrasonic sound signal and based upon a linear pathway for the ultrasonic sound signal from the desired location to the extracorporeal location; and
    accessing the desired location derived from the ultrasonic sound signal by puncturing through tissue from the extracorporeal location with an access needle guided by an ultrasonic probe based on the superimposed line.

6. The method of claim 5, wherein the extracorporeal location comprises a position on a dermis.

* * * * *

UNITED STATES PATENT AND TRADEMARK OFFICE
CERTIFICATE OF CORRECTION

PATENT NO. : 11,998,285 B2
APPLICATION NO. : 17/108244
DATED : June 4, 2024
INVENTOR(S) : Hiroyuki Kojo Page 1 of 1

It is certified that error appears in the above-identified patent and that said Letters Patent is hereby corrected as shown below:

In the Claims

In Column 9, Line 50, in Claim 1, after "comprising:", insert a linebreak

Signed and Sealed this
Nineteenth Day of August, 2025

Coke Morgan Stewart
*Acting Director of the United States Patent and Trademark Office*